United States Patent [19]

Kvasnik et al.

[11] Patent Number: 5,185,521
[45] Date of Patent: Feb. 9, 1993

[54] SENSING APPARATUS AND METHOD FOR DETECTING RAMAN EMISSIONS FROM A SPECIES AT THE INTERFACE OF THE SENSING LENGTH OF AN OPTICAL FIBER

[75] Inventors: Frank Kvasnik, Hyde; Andrew McGrath, Manchester, both of Great Britain

[73] Assignee: Imperial Chemical Industries PLC, London, United Kingdom

[21] Appl. No.: 528,709

[22] Filed: May 24, 1990

[30] Foreign Application Priority Data

May 26, 1989 [GB] United Kingdom ............... 8912219

[51] Int. Cl.$^5$ ................................. H01J 5/16
[52] U.S. Cl. .................. 250/227.23; 356/301
[58] Field of Search ......... 250/226, 227.23, 227.18; 356/301

[56] References Cited

U.S. PATENT DOCUMENTS 4,573,761  3/1986  McLachlan et al.
4,674,878  6/1987  Vo-Dinh.
4,781,458  11/1988 Angel et al. ........................ 356/301
4,823,166  4/1989  Hartog et al. ...................... 356/301

FOREIGN PATENT DOCUMENTS 2571144  4/1986  France.

Primary Examiner—David C. Nelms
Assistant Examiner—T. Davenport
Attorney, Agent, or Firm—Cushman, Darby & Cushman

[57] ABSTRACT

Sensing apparatus based on the use of Raman spectroscopy for detecting the presence and location of a species of interest in a medium comprises a light transmissive optical fibre (4) with an elongate sensing length along at least a portion thereof, a light source means (1) for transmitting pulses of light along the fibre, and a detector (6) for detecting at the same end of the fibre as the light source Raman signals resulting from species (c) of interest at the interface of the sensing length and a medium in which it is located. The time difference between the transmission of an excitation pulse and detection of a Raman emission signal caused by that pulse is determined, and is used to determine the position of the species along the fibre.

19 Claims, 1 Drawing Sheet

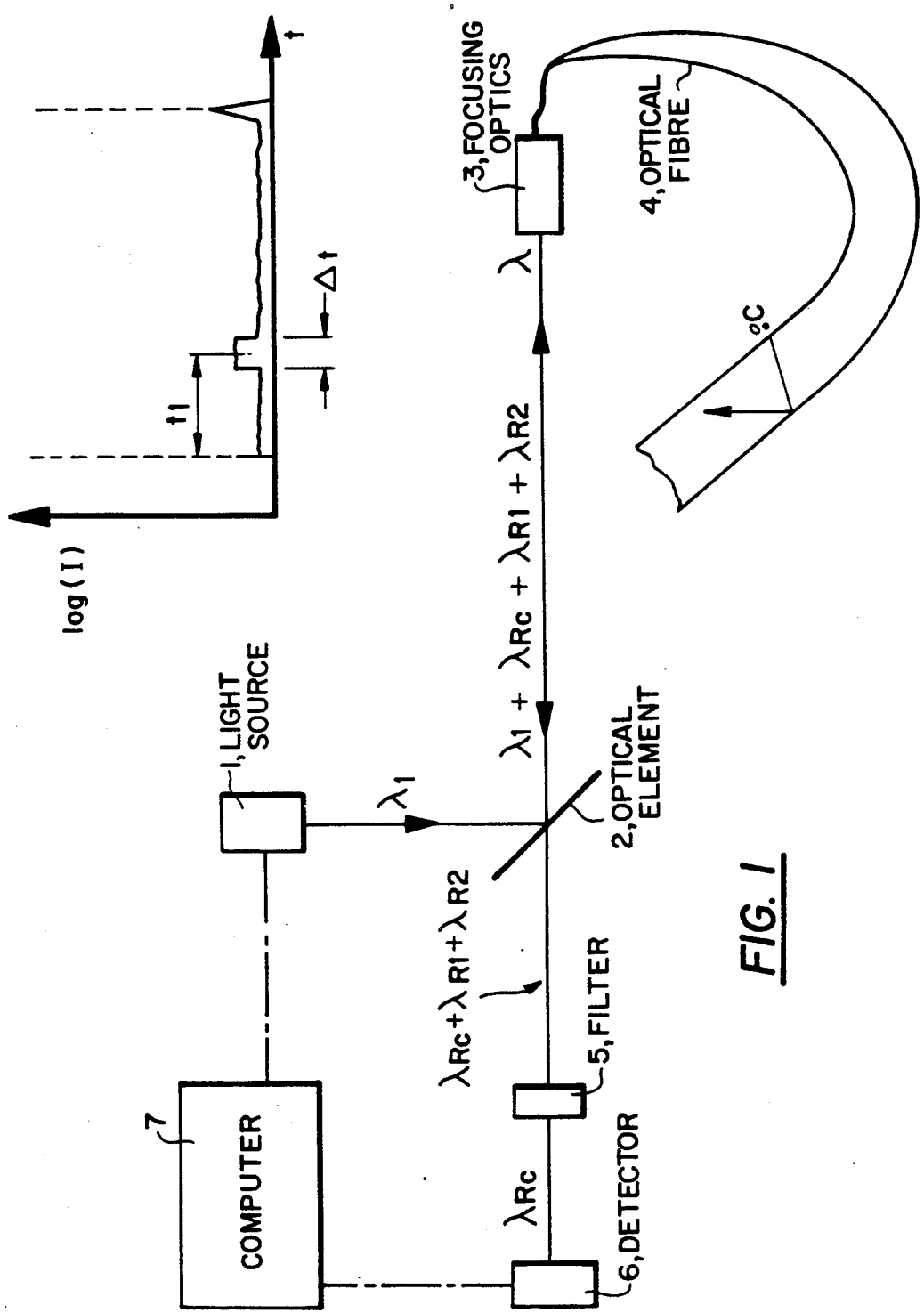

SENSING APPARATUS AND METHOD FOR DETECTING RAMAN EMISSIONS FROM A SPECIES AT THE INTERFACE OF THE SENSING LENGTH OF AN OPTICAL FIBER

BACKGROUND OF THE INVENTION

1. Field of the Invention:

The present invention relates to a sensing apparatus and method based on the use of Raman spectroscopy.

2. Description of the Prior Art:

Raman spectroscopy is a well established technique and the Raman spectra of a multitude of chemical elements and compounds are documented in the literature. A sensing device which makes use of Raman spectroscopy to detect the presence of a particular species in a medium is disclosed in U.S. Pat. No. 4,781,458. This prior device comprises an optical fibre with a light transmissive fibre optic core within a generally opaque cladding, save that over a portion of the fibre the cladding is removed and the exposed core has a coating of a metal. This metal is one which enhances emission of Raman signals of substances adsorbed thereon. The apparatus further comprises a light source and a detector for detecting Raman signals.

In use of this prior apparatus, that portion of the fibre optic core which is coated with the metal is placed in a medium (usually a liquid) in which it is desired to test for the presence of particular species. These species become adsorbed on the metal. Light is shone along the fibre and passes through the thin metal coating. The adsorbed species produce Raman signals which are emitted in all direction, some propagating along the fibre and being detected by the detector. The spectra obtained is characteristic of the adsorbed species, and the intensity of the spectra is indicative of the concentration of the species in the medium.

SUMMARY OF THE INVENTION

According to a first aspect of the present invention there is provided a sensing apparatus comprising a light transmissive optical fibre with an elongated sensing length along at least a portion thereof, a light source means for transmitting pulses of light along the fibre, a detector for detecting at the same end of the fibre as the light source Raman signals resulting from species of interest at the interface of the sensing length and a medium in which it is located, and means for determining the time difference between the transmission of an excitation pulse and detection of a Raman emission signal caused by that pulse, and means for determining from said time difference the position along said fibre at which the species is present.

According to a second aspect of the present invention there is provided a method of detecting the presence and location of a species of interest in a medium comprising providing in the medium a light transmissive optical fibre having an elongate sensing length along at least a portion thereof, transmitting along the fibre pulses of light of a frequency which produces Raman emissions in said species at the interface of the medium and the sensing length, detecting said Raman emission at the same end of the fibre as the light source, determining the time difference between transmission of the excitation pulse and a Raman emission signal caused by that pulse, and determining from said time difference the positions of said species along the fibre.

The term light as used herein covers infra-red and ultra-violet light as well as visible light. The preferred optical sources for use in the invention are those providing light in the visible and near infra-red (e.g. 650-950 mm). The detector is preferably a semi-conductor detector or photomultiplier.

The sensing length of the fibre is that length of the optical fibre which is adapted for sensing the presence of the species of interest. This sensing length may for example be unclad, have a cladding which specifically reacts with a species of interest (e.g. a cladding which enhances emission of Raman signals from the species), or a cladding which is highly permeable to the species of interest.

The sensing length may, for example, be upwards of several metres long and may be provided along a greater length of optical fibre, the remainder of which is clad and serves purely for the transmission of light to and from the sensing length of the fibre.

The positioning of the detector at the same end of the optical fibre as the light source ensures that there will be a time interval between the launch of the excitation pulse into the fibre and the detection of a Raman signal "returned" along the fibre to the detector. Similarly, if the species of interest is at several locations along the sensing length of the fibre there will be a measurable time difference between the individual Raman signals arriving at the detector so that the position of each occurrence of the species along the sensing length may be determined. Furthermore, the concentration of each occurrence of the species may be calculated from the respective Raman signal.

The detection and spatial resolution of the Raman signals may be by means of optical time domain reflectometry technique. In this technique a short pulse of light from a narrow linewidth source such as a laser, is launched into an optical fibre through an appropriate beam splitter. The light propagating along the fibre will be scattered, both elastically (Rayleigh and Mie) and inelastically (Brillouin and Raman), and partially reflected at discontinuities such as fibre joints. Some of the scattered and reflected light will be captured by the optical fibre and will propagate towards the launch end. The majority of the scattered light will originate from the core of the fibre but there will also be a contribution arising from the light-matter interaction with the surrounding medium as described below. A portion of this light will be reflected by the beam splitter towards a wavelength selective element which allows only the Raman signals of interest to reach one or more optical detectors. The distance along the fibre of the species generating the Raman signal can be determined by measuring the time delay between the launch pulse and return signal. A single pulse of light can thus interrogate the whole length of an optical fibre but due to the small magnitude of the return signal it is usual to data average the signal by adding results of many single shots. The time interval between excitation pulses should be such that Raman signals resulting from the previous excitation pulse will have been detected before the next excitation pulse is launched. This time interval will be dependent on the length of the optical fibre. However, the pulsing will generally be at a maximum frequency of 50 kHz.

Light propagating in the core of an optical fibre will give rise to a disturbance, termed the evanescent wave, in the vicinity of the core boundary. Interaction of this evanescent wave with the medium can give rise to a Raman scattered signal a portion of which will be intercepted and captured by the core and guided along the optical fibre. Frequency separations of the Raman lines from the excitation line for a large number of compounds are well known and can be used uniquely to identify species giving rise to this inelastic scattering. In general the frequency separations of these lines are considerably larger than those generated by the material used for the core of the optical fibre. Generally, the Raman signals from species of interest will be greater than about 1600 cm$^{-1}$ and are readily distinguished from signals originating in the fibre itself (which may for example be ca 400 cm$^{-1}$). The invention may for example be used for the detection of ammonia, chlorine, carbon monoxide, and cyanide compounds.

The use of near-infra-red light sources will have the following consequences:

absence of fluorescence signal for the core material which can mask the Raman signals from the cladding/environment;

the evanescent wave will extend further away from the core in accordance with theory;

greater wavelength separation between the Raman and excitation wavelengths, thus reducing the demands on the wavelength discrimination of the detection arrangement;

reduction in the intensity of Raman lines as predicted by theory;

reduced attenuation of the excitation light by the optical fibre;

compact apparatus due to the small size and high efficiencies of the light sources.

On the balance, the use of the near-IR sources would be preferred since it would allow the use of simpler and lower wavelength loss selective systems for the isolation of the desired Raman signals.

Multiple detectors may be used to facilitate a simultaneous multi-element analysis of the surroundings of the optical fibre core.

The intensity of the Raman signal can be greatly enhanced by coating the light transmissions fibre with a thin metallic coating, eg. gold, silver or copper (surface enhanced Raman scattering). Signal enhancement can also be achieved by selecting the excitation wavelength of the light source to be in the vicinity of an absorption band of the species of interest (resonant Raman technique). Alternatively, a chemical reaction between the special cladding material and the anylate, which results in changes in the Raman Spectrum of the cladding material, may be employed for detection purposes. Special claddings can be manufactured from either conventional materials incorporating appropriate reagents or special polymers.

In one particular application of the invention, the optical fibre may be wound around the wall of a chemical reaction vessel and may serve not only to detect the existence of a leak but also its location along the length of the fibre (and hence its position in the vessel).

Similarly, the optical fibre may be provided along the pipeline to detect the location of any leaks. A still further application of the invention is as in a fire detection system. The smoke from the fire includes various gases which may be detected by the Raman emissions and it is thus possible using the sensor of the invention to detect the location of the smoke (and hence the fire).

BRIEF DESCRIPTION OF THE DRAWINGS

The invention will be further described by way of example only with reference to the accompanying drawings, in which:

FIG. 1 represents one embodiment of apparatus in accordance with the invention for detecting a single component;

FIG. 2 is a plot of log(I) vs t for Raman scattering.

DETAILED DESCRIPTION OF THE PRESENTLY PREFERRED EXEMPLARY EMBODIMENT

In the sensing apparatus illustrated in FIG. 1, a pulsed collimated light source 1 generates a beam (wavelength $\lambda_1$) which is directed towards an optical element 2 which has a high reflectivity over a small wavelength range around $\lambda_1$. The beam is reflected by the optical element 2 towards focusing optics 3 (for maximising light throughput through the system) provided at one end of an optical fibre 4. Over its sensing length, the fibre 4 may be either unclad or have a cladding having a Raman Spectrum which changes in a known manner following chemical reaction with a species of interest. In addition this fibre may have a coating which is permeable to species which the sensing apparatus is intended to detect.

Consider now that molecules of a compound C are present at the interface of the fibre 4 and the medium in which it is provided. Assume also that the compound C causes generation of a Raman signal at wavelength $\lambda_{RC}$. A portion of this signal will be propagated back toward the launch end of the fibre together with other scattered wavelengths, including Rayleigh scattering at the excitation wavelength $\lambda_1$, and other scattered signals $\lambda_{R1}$, $\lambda_{R2}$ ... etc.

This scattered signal returns to optical element 2 through which it is transmitted with partial removal of the wavelength $\lambda_1$. After passing through element 2, the signal passes to a filter 5 which allows only transmission of the wavelength $\lambda_{RC}$ which is detected by a detector 6. It will be appreciated that the presence of compound C at several discrete locations along the sensing length of the fibre will result in corresponding signals being detected by the detector 6. The interval between excitation pulses from light source 1 is such that all Raman signals caused by a particular excitation pulse are received by the detector 6 before the next excitation pulse is emitted into the fibre.

The system uses Optical Time Domain Reflectometry Technique for determining the position of compound C along the fibre 4.

The collimated pulsed light source 1 and detector 6 are each associated with a computer 7. Within the computer 7, the time of firing the light from source 1 is recorded together with the time at which the signal $\lambda_{RC}$ is recorded by the detector 6. It is thus possible to compute the distance along the fibre 4 at which the compound C is present.

The time dependence of the returned signals is illustrated in FIG. 2 which is a plot of log (I) vs t (i.e. time) for Raman scattering giving a signal at wavelength $\lambda_{RC}$. The value of $t_1$ is the time between launch of the light pulse and the signal being received by the detector and is representative of the position of compound C along the fibre. The value of $\Delta t$ is representative of the length of the fibre exposed to compound C and to the concentration of the compound. The concentration of compound C in the surrounding medium M can be determined by comparing return signals due to C with that due to M. The peak at the extreme right of the graph is a portion of the Raman signal collected by the fibre and reflected at the end of the fibre and is made up of (1) the signal due to high concentration at t, and (2) integrated signal due to possible low concentrations of compound C along other sections of the fibre.

The invention has been specifically described with reference to the detection of a single compound C, but it will be appreciated that the detection system may be adapted for multi-component detection.

Relative concentrations of multi-compound mixtures can be determined by comparing signals due to each compound $C_1, C_2, C_3, \ldots C_n$ with that arising from the major constituent (e.g. diluant or solvent). Such a comparison will also reduce uncertainties arising from possible localised light losses from the optical fibre when subjected to environmental conditions outside its normal operational region (e.g. severe stress due to tight bends).

We claim:

1. A sensing apparatus comprising:
   a light transmissive optical fibre with an elongated sensing length along at least a portion thereof,
   a light source means for transmitting pulses of light along the fibre,
   a detector for detecting, at the same end of the fibre as the light source, Raman signals resulting from a species of interest at the interface of the sensing length and a medium in which it is located,
   means for determining the time difference between the transmission of an excitation pulse and detection of a Raman emission signal caused by that pulse, and
   means for determining from said time difference the position along said fibre at which the species is present.

2. A sensing apparatus as claimed in claim 1 wherein the light source means is a narrow line width laser.

3. A sensing apparatus as claimed in claim 1 wherein the light source means provides light in the near infra red region of the spectrum.

4. A sensing apparatus as claimed in claim 1 wherein the detector is one of a semi-conductor detector and a photomultiplier.

5. A sensing apparatus as claimed in claim 1 wherein over its sensing length the optical fibre is unclad.

6. A sensing apparatus as claimed in claim 1 wherein over its sensing length the optical fibre has a cladding which undergoes an interaction with the species of interest resulting in a known change in the Raman Spectrum of the cladding.

7. A method of detecting the presence and location of a species of interest in a medium, said method comprising the steps of:
   providing in the medium a light transmissive optical fibre having an elongated sensing length along at least a portion thereof,
   transmitting along the fibre pulses of light of a frequency which produces Raman emissions in said species at the interface of the medium and the sensing length,
   detecting said Raman emission at the same end of the fibre as where the light source is positioned,
   determining the time difference between transmission of the excitation pulse and a Raman emission signal caused by that pulse, and
   determining from said time difference the positions of said species along the fibre.

8. A sensing apparatus as claimed in claim 1, further comprising wavelength selective means for allowing only said Raman signals resulting from the species of interest to reach the detector whereby any contribution from scattered light originating from within a core of the fiber is excluded.

9. A sensing apparatus as claimed in claim 1, wherein the sensing length extends along a major portion of the length of the optical fiber.

10. A sensing apparatus as claimed in claim 9, wherein the sensing length is at least several meters in length.

11. A sensing apparatus as claimed in claim 1, further comprising means for determining the concentration of said species at each location of detection along the length of the sensing element.

12. A method as claimed in claim 7, further comprising detecting the concentration of said species at the locations of detection of the species along the length of the sensing element.

13. A sensing apparatus as claimed in claim 1, wherein the sensing length is deployed externally of a containment enclosure whereby leakage of said species of interest from the containment enclosure, and the location of any such leakage, is detected.

14. A method of detecting the generation of a gaseous species of interest within a zone, comprising the steps of:
   providing a light transmissive optical fiber having an elongated sensing length at least along a portion thereof,
   deploying said optical fiber within the zone,
   interrogating said sensing length by transmitting pulses of light from one end of the optical fiber core along the sensing length, the light having a frequency so as to produce Raman emissions in said species at the interface between the sensing length and said zone,
   detecting said Raman emission at said one end of the fiber,
   determining the time difference between transmission of each pulse and a Raman emission signal generated by that pulse, and
   determining from said time difference the location at which said species is generated along the sensing length.

15. A method of monitoring a zone for the presence of smoke caused by fire, said method comprising the steps of:
   providing a light transmissive optical fiber having an elongated sensing length at least along a portion thereof,
   deploying said optical fiber within the zone,
   interrogating said sensing length by transmitting pulses of light from one end of the optical fiber core along the sensing length, the light having a frequency so as to produce Raman emissions in a gaseous species present in the smoke at the interface between the sensing length and said zone,
   detecting said Raman emission at said one end of the fiber,
   determining the time difference between transmission of each pulse and a Raman emission signal generated by that pulse, and
   determining from said time difference the location at which said species is generated along the sensing length whereby presence of smoke and its location within the zone can be ascertained.

16. A method of detecting the leakage of a predetermined species from a containment enclosure, comprising the steps of:
providing a light transmissive optical fiber having an elongated sensing length at least along a portion thereof,
deploying said optical fiber externally of the containment enclosure,
interrogating said sensing length by transmitting pulses of light from one end of a core of the optical fiber along the sensing length, the light having a frequency so as to produce Raman emissions in said species at the interface between the sensing length and the surroundings,
detecting said Raman emission at said one end of the fiber,
determining the time difference between transmission of each pulse and a Raman emission signal generated by that pulse, and
determining from said time difference the location at which said species is generated along the sensing length.

17. A method as claimed in claim 16, further comprising deriving from said location at which said species is generated along the sensing length, the location at which leakage of said species occurs from the containment enclosure.

18. A method as claimed in claim 16,
wherein the containment enclosure comprises a vessel, and
wherein said sensing length is wound around the vessel.

19. A method as claimed in claim 16,
wherein the containment enclosure comprises a pipeline, and
wherein the sensing length is deployed along the pipeline.

* * * * *